(12) United States Patent
Von Lilienfeld-Toal et al.

(10) Patent No.: US 7,770,473 B2
(45) Date of Patent: Aug. 10, 2010

(54) PRESSURE SENSOR

(75) Inventors: Hermann Von Lilienfeld-Toal, Gelnhausen (DE); Jean-Michel Asfour, Weinheim (DE)

(73) Assignee: Alpha-Fit GmbH, Wurzburg (DE)

( * ) Notice: Subject to any disclaimer, the term of this patent is extended or adjusted under 35 U.S.C. 154(b) by 0 days.

(21) Appl. No.: 12/094,489

(22) PCT Filed: Nov. 23, 2006

(86) PCT No.: PCT/EP2006/011250

§ 371 (c)(1),
(2), (4) Date: Jul. 25, 2008

(87) PCT Pub. No.: WO2007/059971

PCT Pub. Date: May 31, 2007

(65) Prior Publication Data

US 2008/0307899 A1    Dec. 18, 2008

(30) Foreign Application Priority Data

Nov. 23, 2005    (DE) ................ 10 2005 055 842

(51) Int. Cl.
*G01L 1/00* (2006.01)
(52) U.S. Cl. .................................. 73/862.68
(58) Field of Classification Search ............ 73/862.046, 73/862.68
See application file for complete search history.

(56) References Cited

U.S. PATENT DOCUMENTS

| 4,303,733 | A | * | 12/1981 | Bulle et al. ................. 428/367 |
|---|---|---|---|---|
| 4,795,998 | A | | 1/1989 | Dunbar |
| 6,543,299 | B2 | * | 4/2003 | Taylor ................... 73/862.046 |
| 7,276,137 | B2 | * | 10/2007 | Best et al. .................... 162/198 |
| 7,365,031 | B2 | * | 4/2008 | Swallow et al. ............. 442/181 |
| 7,484,408 | B2 | * | 2/2009 | Healey ........................ 73/149 |
| 7,544,627 | B2 | * | 6/2009 | Tao et al. .................... 442/189 |
| 2002/0194934 | A1 | | 12/2002 | Taylor |
| 2003/0119391 | A1 | * | 6/2003 | Swallow et al. ................ 442/6 |
| 2005/0054941 | A1 | * | 3/2005 | Ting et al. ................... 600/529 |
| 2005/0109587 | A1 | * | 5/2005 | Best et al. ............. 198/810.01 |
| 2005/0282009 | A1 | * | 12/2005 | Nusko et al. ................ 428/375 |

FOREIGN PATENT DOCUMENTS

| DE | 103 14 211 A1 | 11/2003 |
|---|---|---|
| DE | 10 2004 025237 A1 | 3/2005 |
| EP | 0 267 544 A2 | 5/1988 |
| EP | 1 507 040 A | 2/2005 |
| WO | WO98/33193 | 7/1998 |
| WO | WO 2005/000052 | 1/2005 |

* cited by examiner

*Primary Examiner*—Lisa M Caputo
*Assistant Examiner*—Freddie Kirkland, III
(74) *Attorney, Agent, or Firm*—Barnes & Thornburg LLP

(57) ABSTRACT

The invention relates to a pressure sensor which can be incorporated into textile products. The pressure sensor includes a multilayer thread having a pressure sensitive layer exhibiting a pressure-dependent electrical resistance, and a conductive layer in contact with the pressure sensitive layer. Further, the sensor includes conductive threads in contact with the multilayer thread.

9 Claims, 3 Drawing Sheets

PRESSURE SENSOR

CROSS-REFERENCE TO RELATED APPLICATIONS

This application is a National Phase Application based upon and claiming the benefit of priority to PCT/EP2006/011250, filed on Nov. 23, 2006 which is based upon and claims the benefit of priority to German Application 10 2005 055 842.9, filed on Nov. 23, 2005, the contents of which are incorporated herein by reference.

BACKGROUND OF THE INVENTION

The invention relates to a pressure sensor and a textile product including the sensor.

DE 10314211 A1 discloses a sock having a pressure sensor to measure the pressure distribution around the foot of, e.g., a diabetic patient. The measurement is used in the adaptation of a shoe to the patient's foot so as to avoid pressure peaks which would lead to tissue damage (diabetic foot syndrome). The sock includes a matrix of metallic fibers incorporated into the fabric of the sock. The metallic fibers are connected to an electronic circuit which computes the pressure distribution from the electric resistances at the intersections between the metallic fibers.

WO 2005/000052 A2 discloses a pressure sensitive input interface for an electronic device. The interface is incorporated into a textile garment and includes an array of conductive and non-conductive fibers.

It has been found that the textile pressure sensors known in the art do not allow precise measurement of an applied pressure over a sufficiently wide range. Instead, they exhibit essentially an on-off behavior where the electric resistance between the conductive drops sharply at a pressure threshold when the conductive come into contact with each other. But the resistance does not change significantly below or above the pressure threshold. Moreover, the pressure threshold is difficult to control and depends on hysteresis effects.

WO 98/33193 discloses a polymer composition showing an electrical resistivity which depends on distortion forces. The composition comprises conductive particles embedded in a non-conductive polymer.

SUMMARY

It is an object of the invention to provide a pressure sensor which is compatible with textile production processes such as weaving, knitting, warp knitting or sewing and which gives precise and reliable pressure or force measurement results.

This object is solved by the pressure sensor of claim 1. The dependent claims relate to preferred embodiments of the invention and to textile products including the pressure sensor.

The pressure sensor of the invention has the advantage that the electric response on the applied pressure depends primarily on the response of the pressure sensitive layer in the multilayer thread, rather than on the contact resistance between the conductive threads. Thus, the sensor can give precise and reliable pressure or force measurement results.

BRIEF DESCRIPTION OF THE DRAWINGS

The accompanying drawings are representations of preferred embodiments of the invention, wherein.

DETAILED DESCRIPTION

In the following description, like elements throughout the different embodiments are designated by like reference numbers.

Figure 1:
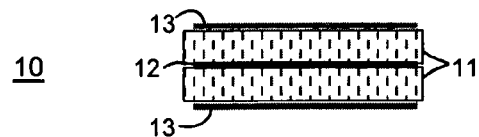
FIG. 1 shows a cross-sectional view of a laminated film used in a pressure sensor of a first embodiment of the invention.
Figure 2:
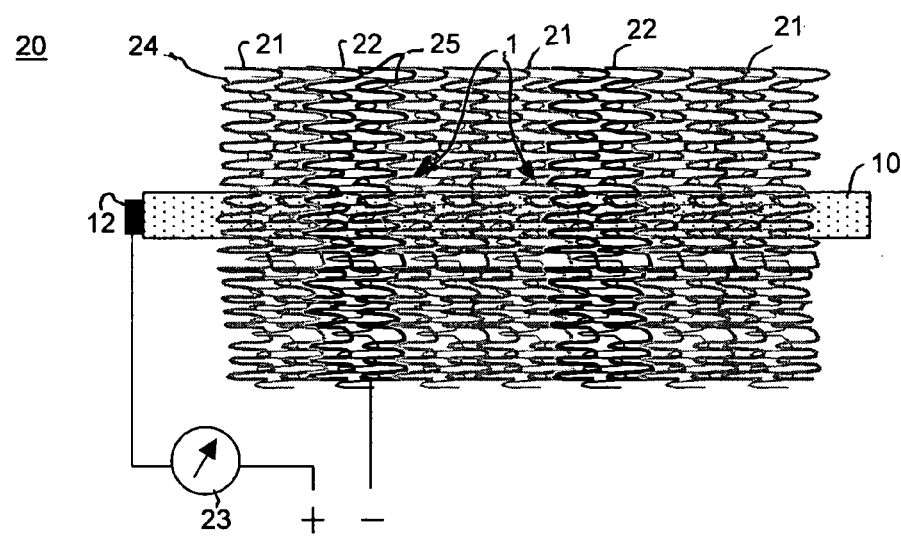
FIG. 2 shows a plan view of a textile pressure sensor using the laminated film of FIG. 1.

A textile pressure sensor in accordance with a first embodiment of the invention is shown in FIGS. 1, and 2. This sensor includes a multilayer thread being a fine strip of laminated film 10, incorporated into a fabric 20.

FIG. 1 shows a cross-sectional view of the laminated film 10. The laminated film 10 comprises a core made of an electrically conductive layer 12. Both surfaces of the conductive layer 12 are covered by pressure sensitive layers 11.

The outer surfaces of the pressure sensitive layers 11 are covered by electrically conductive electrode layers 13. The pressure sensitive layers 11 are made of an electrically conductive elastic material that shows a pressure-dependent resistance between the conductive layer 12 and the electrode layers 13. The material may be a conductive polymer like polyaniline. Another preferred material is an elastic insulator such as silicone, including conductive filler particles such as carbon black particles. As an alternative, the pressure sensitive layers 11 may also be made of piezoelectric material.

As shown in FIG. 2, a finely cut strip of the laminated film 10 of FIG. 1 is incorporated as a filler thread into a knitted fabric 20. The fabric 20 includes electrically nonconductive zones 21 and electrically conductive zones 22 which are arranged alternating and each extend perpendicular to the laminated film 10. The non-conductive zones 21 are made from warp threads 24 that are non-conductive. The electrically conductive zones 25 are made at least partly from warp threads 25 that are electrically conductive. The conductive threads 25 are preferably thin metal wires. The outer surfaces of the laminated film 10 are substantially covered by the fabric 20 formed of the threads 24, 25, so that the conductive threads 25 make good contact with the electrodes 13 on both surfaces of the film 10. Thus, the electric resistance between a conductive zone 22 and the core 12 of the laminated film 10 is closely related to the forces of pressure acting perpendicular to the plane of the fabric 20 and thus related to the pressure acting on the pressure sensitive layers 11 in the region 1 of intersection between the film 10 and the conductive zone 22. A measurement device 23 connected to the core 12 and the conductive threads 25 of the conductive zone 22 can measure the pressure at the intersection region 1. Multiple such measurements for different ones of such conductive zones 22 yield pressure values for different ones of such intersection regions 1 and show the pressure distribution along the strip of laminated film 10.

In a modification of the embodiment shown in the FIG. 2, a plurality of laminated films 10 are disposed in parallel spaced apart from each other, to allow the measurement of a two-dimensional distribution of pressure on the surface of the fabric 20.

Figure 3:
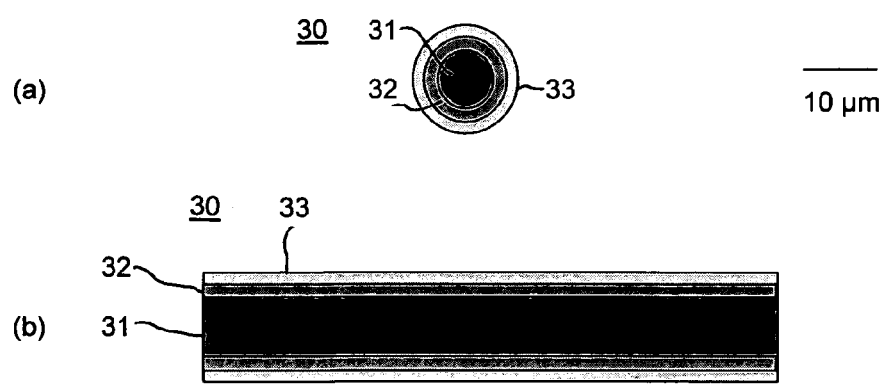
FIG. 3 shows transverse and longitudinal cross-sectional views of a multilayer thread used in a pressure sensor of a second embodiment of the invention.
Figure 4:
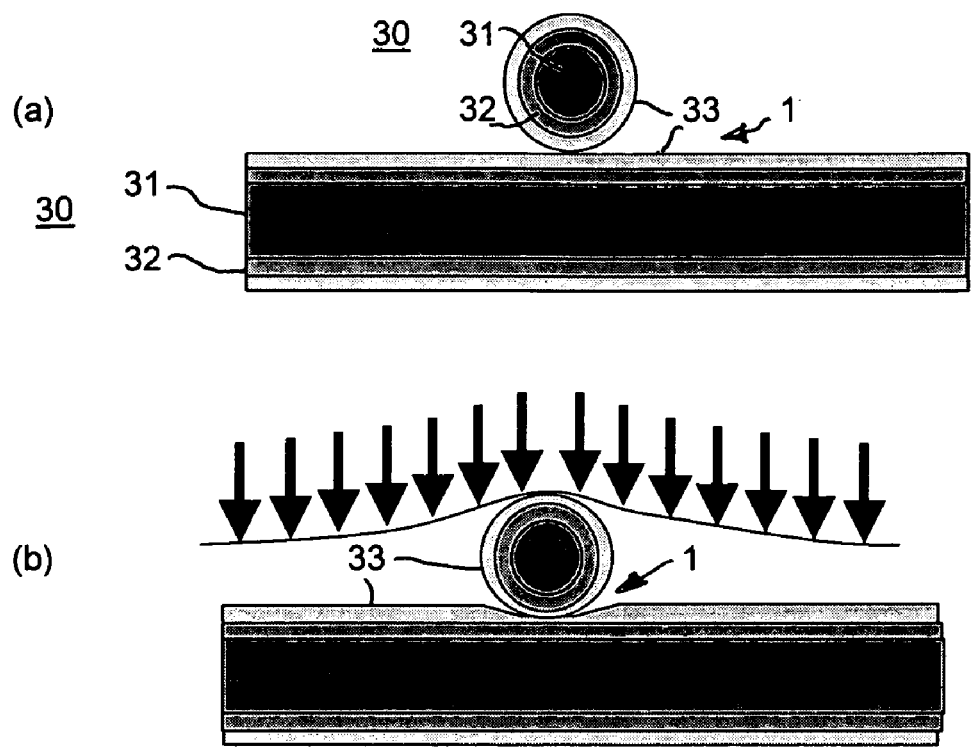
FIG. 4 shows cross-sectional views of a textile pressure sensor using an arrangement of the multilayer threads of FIG. 3.

FIGS. 3 and 4 show a second embodiment of the invention. In this embodiment, multilayer threads 30 as shown in FIG. 3 replace the strip of laminated film 10 of the first embodiment and also act as conductive wires to replace the metal wires 25 of the first embodiment.

FIG. 3(*a*) shows a transverse cross-section of the multilayer thread 30 and FIG. 3(*b*) shows a lengthwise cross-section thereof. The multilayer thread 30 comprises a non conductive polymer fiber 31 covered by a conductive coating 32, which, in turn, is covered by an elastic pressure sensitive coating 33. The conductive coating 32 may be a metal coating (e.g. aluminum, copper or, preferably, silver) applied by an electrochemical process. The pressure sensitive coating 33 may be made of a conductive elastic polymer applied by immersion of the thread 30 in a solution of the elastic polymer. An example of the polymer is polyaniline. Another example of the pressure sensitive coating 33 is an elastic insulator layer such as silicone including conductive filler particles such as carbon black particles.

FIG. 4(*a*) shows a cross-sectional view of the fabric at an intersection region 1 between two of the multilayer threads 30 of FIG. 3. FIG. 4(*b*) shows the same view but upon application of pressure in a direction perpendicular to the plane of the fabric, as indicated by arrows in the Figure. As can be seen, the pressure leads to elastic compression of the pressure sensitive coating 33 in the intersection region 1 where two multilayer threads 30 intersect and contact each other. Compression of the pressure sensitive coatings 33 results in a reduction of the distance between the conductive coatings 32 of the two multilayer threads 30, and thus in a resistance for the electric current across the pressure sensitive coatings 33 between the two threads 30 which decreases in accordance with an increasing pressure applied. Thus, the pressure can be measured by means of a measurement device 23 measuring the electric resistance in the way shown in FIG. 2.

Figure 5:
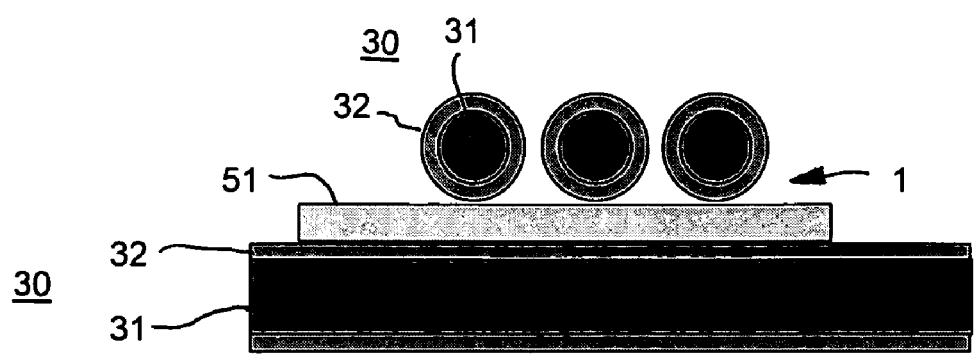
FIG. 5 shows another pressure sensor as a third embodiment of the invention.

FIG. 5 shows a third embodiment which differs from the second embodiment in that the multilayer threads 30 lack the pressure sensitive coating and, instead, a strip of pressure sensitive film 51 is interposed between the threads 30 at their intersection regions 1. Preferably, the strip of pressure sensitive film 51 is incorporated into the textile fabric as a filler thread running in parallel to at least one of the threads 30. The pressure sensitive film 51 exhibits an electric resistance which depends on its thickness. Thus, when being compressed under the application of pressure, the electric resistance measured between intersecting threads lowers just as in the first and second embodiments. The pressure sensitive film 51 may be made of the same elastomeric material as the pressure sensitive coating 33 but may be thicker.

Figure 6:
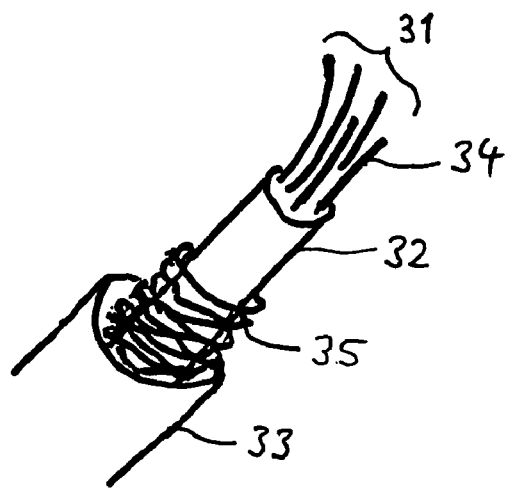
FIG. 6 shows a more detailed representation of the multilayer thread of FIG. 3.

FIG. 6 shows the structure of the multilayer thread 30 of the second embodiment in more detail. The polymer fiber 31 forming the core of the thread comprises a multitude of filaments 34. The core is coated by the conductive coating 32 made of a good conductor, preferably a metal such as aluminum, copper or, preferable, silver. The conductive coating 32 is, in turn, covered by a pressure sensitive coating 33 made of an elastic material having an electric resistivity in between that of a good conductor such as a metal, and that of an insulator. It may be made of a conductive polymer such as polyaniline, or of an insulating polymer or elastomer containing conductive filler particles, such as silicone containing carbon black particles. Thus, the electric resistance measured in radial direction of the thread 30 between the conductive coating 32 and the outer surface of the pressure sensitive coating 33 depends on the thickness of the pressure sensitive coating 33 and thus on the degree the elastic polymer coating 33 is compressed by the forces of pressure acting on the thread. To prevent a hysteresis in the dependency of the electric resistance on the pressure, a fiber 35 is wound around the conductive coating 32 underneath the pressure sensitive coating 33. The fiber 35 stabilizes the shape of the thread 30 and helps it to return to its original shape after deformation under temporary application of pressure. The density of the windings of the fiber 35 is sufficiently low so as to leave gaps between the windings, through which the conductive coating 32 and the pressure sensitive coating 33 maintain in firm contact with each other. If no such gaps are provided, the fibre fiber 35 should be made of a good conductor such as a metallic wire.

Figure 7:
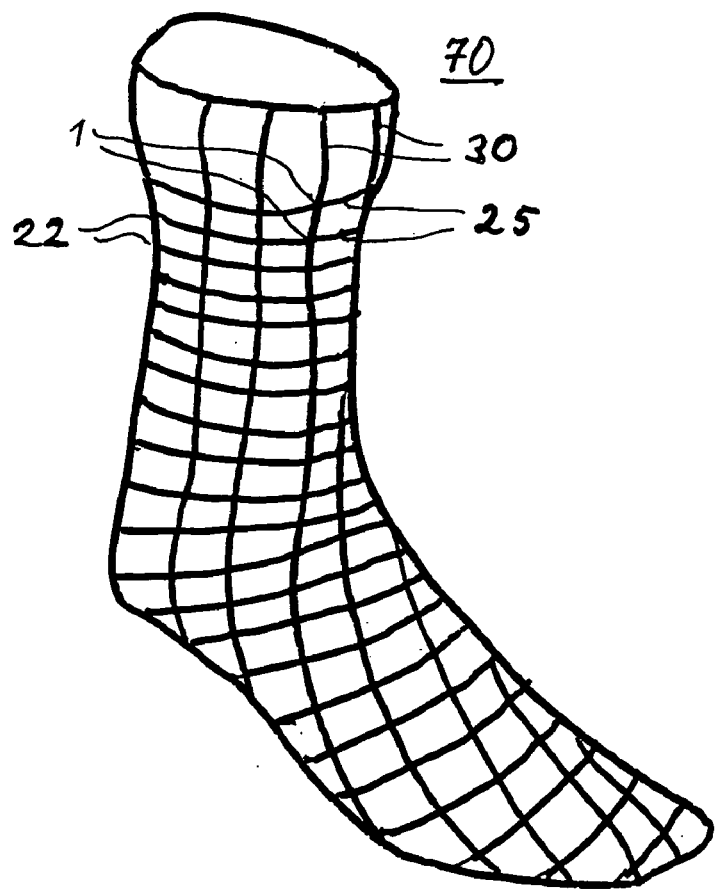
FIG. 7 shows a sock including a textile pressure sensor having the multilayer threads of FIG. 3 in a fourth embodiment of the invention.

FIG. 7 shows a sock 70 as an example of a garment incorporating a pressure sensor in accordance with a fourth embodiment of the invention. The sock 70 is made of a knitted fabric mainly consisting of insulating yarn such as cotton, wool or synthetic fiber. Incorporated into the fabric are filler threads extending in longitudinal direction spaced apart and parallel to each other. The filler threads are made of the multilayer threads 30 shown in FIGS. 3 and 6. Further incorporated into the fabric are warp threads made of conductive: threads 25 which extend in generally horizontal, direction of the sock along spaced apart conductive zones 22 in the way as shown in FIG. 2. Thus, the fabric of the sock 70 resembles that of FIG. 2 except that the strip of laminated film 10 of the FIG. 2 embodiment is replaced by a multilayer thread 30 of the FIG. 3 embodiment.

When the conductive threads 25 and the multilayer threads 30 are connected to an electronic circuit as disclosed in DE 103 14 211 A1, the circuit can precisely measure the pressure at each of the intersection regions 1 where the conductive threads 25 and multilayer threads 30 intersect each other. The circuit then generates a three-dimensional image of the sock 70 with the pressure value acting on the surface of the sock 70 at each of the intersection regions 1 visualized by different shades of grey or by different colors.

The embodiments described above may be used to:

measure pathologic pressure peaks at the foot of a diabetic patient and thus help to prevent the diabetic foot syndrome, measure pressure distributions during adaptation of a prosthesis to a patient, measure the pressure distribution on a mattress and thus help to avoid tissue damage in patients who have to lie over prolonged periods of time, measure physiological pressures in controlling breathing and artificial respiration, controlling blood pressure and heartbeat in a textile blood pressure measuring sleeve, and measuring the forces exerted by stockings such as compression hosiery, monitor forces acting on the human body during activities such as prolonged seating or sports (walking, running, bicycle-riding, horse-riding), assist in the adaptation of shoes to an individual person, in particular in cases where the person cannot tell herself or himself whether a shoe fits or where a more perfect fit is essential such as in the adaptation of sports shoes, skiing boots etc. to individual athletes, and measure forces and pressures in technical apparatus or robots.

In the embodiments described above, a first plurality of laminated strips 10 or multilayer threads 30 are arranged to intersect a second plurality of conductive threads 25 or multilayer threads 30, so as to form a fabric 20 having an array of spaced apart intersection regions 1 where the pressure acting in thickness direction of the fabric can be measured. However, laminated strips 10 or multilayer threads 30 on the one hand and conductive threads 25 or multilayer threads 30 on the other hand may also be incorporated in parallel to each other into a textile product such as a rope. The electric resistance between them will then be a measure for the compressive pressure acting on the rope, i.e. the pressure integrated along the length of the rope. A rope of this kind incorporated into a mechanical structure such as a building, vehicle tire or other vehicle part is useful to measure the load acting on the part and to monitor its structural integrity. A rope of this kind may also be integrated into textile products such as compression hosiery to monitor their effectiveness.

The invention claimed is:

1. A pressure sensor comprising a plurality of conductive threads, wherein
    at least one of said conductive threads is a multilayer thread in contact with other said conductive threads and includes a pressure sensitive layer having a pressure-dependent electric characteristic, and
    said multilayer thread includes a non-conductive fiber covered by a conductive coating overlaid by said pressure sensitive layer,
    wherein said pressure sensitive layer of said multilayer thread is in electric contact with said other conductive threads.

2. The pressure sensor of claim 1, wherein the pressure sensor is incorporated in a fabric including parallel zones which contain said other conductive threads and are spaced apart by non-conductive zones, each of said parallel zones and non-conductive zones intersecting the multilayer thread so as to form an array of discrete regions where the multilayer thread and said other conductive threads intersect each other.

3. The pressure sensor of claim 2, wherein the fabric is made by knitting the non conducting threads and said other conductive threads as warp threads, and further includes said multilayer thread as a filler thread.

4. The pressure sensor of claim 2, further comprising a plurality of said multilayer threads are provided so as to extend in parallel to and being spaced apart from each other, so as to form a two-dimensional array of discrete regions where the multilayer threads intersect said other conductive threads.

5. The pressure sensor of claim 1, comprising a rope made of said multilayer threads, said other conductive threads and non-conductive threads.

6. The pressure sensor of claim 1, wherein said multilayer thread is implemented as a strip of laminated film.

7. The pressure sensor of claim 1, wherein a plurality of further said multilayer threads are used for said other conductive threads.

8. A garment including a pressure sensor in accordance with claim 1.

9. A sock including a pressure sensor in accordance with claim 1.

* * * * *